United States Patent [19]

Warren et al.

[11] Patent Number: 4,693,790
[45] Date of Patent: Sep. 15, 1987

[54] METHOD FOR MONITORING THE QUALITY OF ZNSO₄ ELECTROLYTE CONTAINING SB (V)

[75] Inventors: Ian H. Warren, Richmond; Felix Mok, Vancouver, both of Canada

[73] Assignee: Cominco, Ltd., Vancouver, Canada

[21] Appl. No.: 805,297

[22] Filed: Dec. 5, 1985

[30] Foreign Application Priority Data

Sep. 12, 1985 [CA] Canada ................................. 490589

[51] Int. Cl.⁴ ............................................ G01N 27/46
[52] U.S. Cl. .................................... 204/1 T; 204/119; 204/434
[58] Field of Search ............... 204/434, 1 T, 114, 115, 204/116, 117, 118, 119

[56] References Cited

U.S. PATENT DOCUMENTS 4,324,621  4/1982  Kerby .................................. 204/1 T
4,479,852  10/1984  Bindra et al. ....................... 204/1 T

FOREIGN PATENT DOCUMENTS 988879  5/1976  Canada ................................. 204/114

OTHER PUBLICATIONS

M. Maja et al., J. Electrochem. Soc., Electrochemical Tech., p. 1538, Sep. 1971.
Chem. Abs., vol. 69, p. 4269, 45410z, (1968).
Digby D. MacDonald, "Transient Techniques in Electrochemistry, pp. 33-37, (1977).
Charles L. Mantell et al, Trans. Metallurgical Soc. AIME, vol. 236, p. 718, May 1966.
Herbert S. Jennings et al., Metallurgical Trans., vol. 4, p. 921, Apr. 1973.
Oystein Vennesland et al., Acta Chem. Scand., 27, No. 3, pp. 846-850, (1973).
T. N. Andersen et al., Metallurgical Trans. B, vol. 7B, p. 333, (1976).
A. D'Este and R. Guerriero: Montevecchio 16, Nos. 3-4, 1-11 (1965). (Also identified as #6A).
T. R. Ingraham and R. C. Kerby, Can. Met. Quart., 11, 2, 451-454 (1972).
D. C. Grahame, J. Phys. Chem., 57, 3, 257-261 (1953).

*Primary Examiner*—T. Tung
*Attorney, Agent, or Firm*—Wenderoth, Lind & Ponack

[57] ABSTRACT

Certain continuous methods for monitoring the quality of ZnSO₄ electrolyte lose sensitivity when the electrolyte contains Sb (V). The sensitivity can be increased by electrochemically reducing Sb (V). A sample of electrolyte which contains impurities including Sb (V) and which may also contain polarization affecting agents is passed through a test cell containing an elongated moving cathode having a predetermined area exposed to the electrolyte, an anode and a reference electrode. A substantially constant current in the range of 0.01 to 0.20 A/cm² is applied to the electrodes and the cathode is moved with a speed sufficient to obtain measured values of the cathode polarization potential of zinc deposition on zinc. The measured values are related to the concentrations of impurities, polarization affecting agents, or both and to the concentration ratio between impurities and polarization affecting agents, and the process for zinc recovery is adjusted in response to these relations to obtain optimum zinc recovery.

16 Claims, No Drawings

METHOD FOR MONITORING THE QUALITY OF ZNSO₄ ELECTROLYTE CONTAINING SB (V)

BACKGROUND OF THE INVENTION (a) Field of the Invention

This invention relates to a method for continuously monitoring the quality of zinc sulfate electrolyte containing Sb (V)and, more particularly, to a method for measuring the cathode polarization potential of zinc deposition and controlling the electrolyte purification and electrowinning processes in response to deviations of recorded values of the potential from the desired values.

In the process for electrowinning zinc from zinc sulfate solutions, impurities such as antimony, germanium, copper, nickel, cobalt, iron, cadmium and lead, when present above certain critical concentrations, cause re-solution of deposited zinc and a corresponding decrease in the current efficiency of the zinc deposition. To reduce the concentration of impurities in electrolyte, a complex purification procedure, which generally includes an iron oxide precipitation and a zinc dust treatment, is employed prior to electrolysis, In addition to the purification, polarizing additives such as glue may be added to the electrolyte to reduce the effects of the remaining impurities and to provide smooth and level deposits.

(b) Description of the Prior Art

The prior art contains a number of references related to methods for determining the effects of impurities, glue and other addition agents on electrodeposition processes for metals, and for determining the purity of zinc sulfate solutions.

Such methods are disclosed by C. L. Mantell et al (Trans. Met. Soc. of AIME, 236, 718–725, May 1966), H. S. Jennings et al (Metallurgical Transactions, 4, 921–926, April 1973), O. Vennesland et al (Acta Chem. Scand., 27, 3, 846–850, 1973), T. N. Anderson et al (Metallurgical Transactions B, 7B, 333–338, September 1976), M. Maja et al (J. Electrochem. Soc., 118d, 9, 1538–1540, 1971) and P. Benvenuti et al (La Metallurgia Italiana, 60, 5, 417–423, 1968); and in Can. Pat. No. 988,879 and U.S. Pat. Nos. 3,925,168, 4,146,437, 4,132,605, 4,406,753, 4,217,189, 4,324,621, and 4,443,301.

Although a number of methods disclosed in the prior art make it possible to continuously monitor and control the quality of electrolytes by means of a moving cathode, the sensitivity of these methods can be seriously affected under certain conditions. More specifically, when applied to zinc sulfate electrolyte used for the electrowinning of zinc, the sensitivity of the method is decreased or lost when the electrolyte contains antimony in the pentavalent state. The presence of Sb (V) in the electrowinning process is due to the high oxidation potential of the electrolyte which contains typically $Mn^{3+}$ and $MnO_4^-$ ions. Sb (V) can also be present in certain materials occurring in the process for the recovery of zinc and used in the preparation of electrolyte which results in the presence of Sb (V) in the purification process.

SUMMARY OF INVENTION

We have now found that the loss of sensitivity of the monitoring method using electrolyte containing Sb (V) can be overcome economically and efficiently by carrying out the reduction electrochemically in a test cell operated with a moving cathode and at a relatively high current density. More specifically, we have found that by measuring the cathode polarization potential for zinc deposition on a continuously moving elongated cathode at a substantially constant current, the quality of the electrolyte can be monitored and controlled without loss of sensitivity due to the presence of antimony (V).

The method and apparatus of the invention apply to zinc sulfate solutions which are obtained in processes for the treatment of zinc containing materials such as ores, concentrates, etc. These treatment processes include thermal treatments and hydrometallurgical treatments such as roasting, leaching, in situ leaching, bacterial leaching and pressure leaching, Such solutions, which are referred to in this application as zinc sulfate electrolyte, may be acidic or neutral solutions.

When zinc sulfate electrolyte containing Sb (V) and containing impurities, or polarization affecting agents, or both, is subjected to a plating current applied to electrodes, including a cathode, an anode and a reference electrode, placed in a test cell containing electrolyte and the current has a value which is sufficient to cause deposition of zinc on a cathode made of a suitable metal which is covered with deposited zinc, the value of the resulting cathode potential can be measured. This cathode potential, when corrected for the value of the IR voltage drop between the reference electrode and the cathode and for the value of the reversible potential of zinc in the electrolyte, is hereby defined as the cathode polarization potential (called cpp hereafter) for zinc deposition on zinc. When the cathode is a continously moving cathode, values of the cpp can be measured and recorded and the purification process of zinc sulfate electrolyte and the electrowinning process of zinc from zinc sulfate electrolyte can then be controlled in response to the measured and recorded values of the cpp, whereby the sensitivity of the method is increased in the presence of Sb (V). The measured values of the cpp can be used as a direct measure of the concentrations of impurities, of concentrations of polarization affecting agents and of concentrations of such agents relative to the impurity concentrations in the electrolyte in the process for the recovery of zinc which includes the purification process and the electrowinning process. In response to measured values of the cpp, the effectiveness of the purification and electrowinning processes can be monitored and controlled. The purification process can be adjusted by adjusting the impurity concentration while the electrowinning process can be adjusted by adjusting the concentration of polarization affecting agents, or impurities, or both, relative to each other in the electrolyte, so that optimum current efficiency and level zinc deposits are obtained in the electrowinning process.

Accordingly, there is provided a method for monitoring a process for the recovery of zinc using a zinc sulfate electrolyte and containing concentrations of impurities, including pentavalent antimony, said method having sensitivity to pentavalent antimony and comprising the steps of establishing a test circuit comprising a test cell, a sample of electrolyte, an elongated moving cathode made of an electrically conductive material on which zinc is deposited which elongated moving cathode is immersed in and passes through said sample and has a predetermined area exposed to said electrolyte, an anode and a reference electrode being immersed in said sample, the electrodes being removably positioned in the test cell in fixed relation to one another, a constant current supply and a voltage measuring means electrically connected to said electrodes; applying a substantially constant current to the electrodes in said test cell, said current corresponding to a current density in the range of about 0.01 to 0.20 A/cm² based on the exposed area of the cathode and being sufficient to cause the exposed area of the cathode to become fully covered with deposited zinc; measuring the cathode polarization potential of zinc deposition on said cathode; moving said cathode at a speed sufficient to obtain measured values of the cathode polarization potential for zinc deposition onto zinc; the sensitivity being expressed in a sensitivity factor, said factor being in the range of about 0.5 to 4.0 and defined by the following equation:

Sensitivity Factor = $I \times L/S$, wherein:
  I represents current density, A/cm²;
  L represents the immersed length of the cathode exposed to electrolyte, cm; and
  S represents the speed of the moving cathode, cm/min;

relating values of the measured cathode polarization potential to the concentrations of impurities in said sample; and adjusting the process for the recovery of zinc to obtain optimum recovery of zinc.

In other embodiments, the electrolyte also contains oxidized manganese species and at least one polarization affecting agent, and values of the measured cathode polarization potential are related to the concentration of that agent or to the concentration ratio between impurities and agent(s), and the concentration of the agent or the concentration ratio is adjusted to obtain optimum efficiency and level metal deposits in the process of the recovery of zinc.

DESCRIPTION OF THE PREFERRED EMBODIMENTS

The invention will now be described in detail. The apparatus used in the method for measuring the cpp of zinc consists of a test circuit which comprises a test cell, a sample of zinc sulfate electrolyte, an elongated moving cathode, an anode, a reference electrode, means to supply a constant current and means for measuring the cpp. The test cell is a small container of circular, square or rectangular cross-section made of a suitable material resistant to acid zinc sulfate electrolyte and large enough to hold a suitable sample of electrolyte. Means are provided in the cell to make it possible to continuously add electrolyte to and to discharge electrolyte from the test cell. The three electrodes are immersed in the electrolyte sample and are removably positioned in the cell at constant distances from each other.

The elongated moving cathode is preferably made of a suitable electrically conductive metal or metal alloy in the shape of a strip, wire, or foil on which zinc can be electro-deposited. Amongst suitable metals are aluminum, aluminum alloys, steel, titanium and zinc.

The elongated moving cathode is preferably made of aluminum or aluminum alloy wire, foil or strip which moves through the electrolyte sample in the test cell. The cathode wire, strip or foil is pulled through the electrolyte around a horizontally positioned, rotatable pulley which is partly immersed in the electrolyte sample in the test cell. For a given diameter and a given degree of immersion of the pulley, a substantially constant surface area of the elongated moving cathode is exposed to the electrolyte sample. Means are provided to pull the cathode intermittently or continuously through the electrolyte. Preferably, these means include provisions to move the cathode continuously at a constant rate. The use of a moving elongated cathode made of aluminum or aluminum alloy wire, foil or strip has a number of advantages. No special preparation of the aluminum surface is necessary, aluminum or aluminum alloy wire, foil or strip is readily available at low cost and test results are reproducible. The elongated moving cathode does not have to be replaced or cleaned and thus allows intermittent or continuous operation, while the used portion is discarded. Most commercially available aluminum and aluminum alloys in the form of wire, foil and strip are suitable, as long as they have sufficiently smooth and clean surfaces and have electrochemical characteristics that produce reproducible test results. The use of an elongated moving cathode is preferred over the use of a disc- or cylindrical-type rotating cathode which requires the removal of deposited zinc. Such removal affects the reproducibility of the measurements in a continuous monitoring system. The need for removal of deposited zinc also adds unnecessarily to the complexity and costs of the method.

The anode is made of a suitable material such as, for example, platinum, platinum-coated titanium, or lead-silver alloy. The reference electrode can be any one of a number of suitable reference electrodes such as, for example, a standard calomel electrode (SCE).

The three electrodes are electrically connected to a source of substantially constant current and to voltage measuring means for the cpp. The source of constant current is connected to the anode and the elongated moving cathode. The voltage measuring means for the cpp measures the cathode potential on the elongated moving cathode relative to the reference electrode, corrects for the value of the IR voltage drop between the reference electrode and the cathode and for the value of the reversible potential of zinc in the electrolyte, and thereby provides values of the measured cpp. The measured cpp may, for example, be recorded on a meter or other suitable read-out instrument, or alternatively, may be recorded in the form of a line or trace as a function of time. The electrodes are removably positioned in the cell in fixed relation to each other. Good results are obtained, for example, when the surface area of the moving cathode that is in contact with electrolyte is kept at a fixed distance of about 4 cm from the surface of the anode and when the reference electrode is positioned between the cathode and the anode in such a way that the tip of the reference electrode is rigidly located at a distance of about 1 cm from the moving cathode.

Suitable means may be provided to maintain the electrolyte in the cell at a suitable constant temperature.

In the method of the invention, a sample of acidic or neutral zinc sulfate electrolyte, which contains Sb (V) is added to the test cell. When the sample is obtained from the electrowinning process, the sample usually also contains at least one polarization affecting agent and oxidized manganese species. A sample obtained from the electrowinning process has an oxidation potential which is typically in excess of one volt versus SCE. To ensure reproducible results, the sample is kept in motion by agitation or circulation and, preferably, by continuously passing a small flow of electrolyte through the test cell. Electrolyte added to the cell may be adjusted to a certain zinc or zinc and acid content, such as, for example, 55 g/L zinc and 150 g/L sulfuric acid, in order to minimize any variation that may be caused by variations in zinc and/or acid concentrations in the electrolyte. It is to be understood, however, that concentrations in the range of 1 to 250 g/L zinc and 0 to 250 g/L sulfuric acid are equally satisfactory.

The elongated moving cathode is pulled through the electrolyte sample intermittently or continuously at a speed sufficient to obtain values of the cpp for the deposition of zinc onto zinc, whereby the surface area of the cathode exposed to the electrolyte becomes fully covered with deposited zinc. Preferably, the moving cathode is advanced continuously at a constant speed.

A current is applied to the anode and the moving cathode to cause deposition of zinc onto the cathode. At low values of the applied current, the cathode would only be partially covered with deposited zinc and values of the nucleation overpotential or activation overpotential would be measured, such as known from prior art methods. At such low values of the current, the prior art methods have a much reduced sensitivity in the presence of Sb (V) and are insensitive when the electrolyte has a high oxidation potential and contains Sb (V), although the methods have normal or high sensitivity in the presence of Sb (III). When Sb (V) is present, however, we have found that the methods can only be made sensitive when the Sb (V) is transformed, by either chemical or electrochemical reduction. We have established that chemical reduction may be carried out, when Sb (V) and oxidized manganese species are present, in one or two stages using reductants for oxidized manganese species such as hydrazine, sulfur dioxide, zinc sulfite, sodium - sulfite - thiosulfate, or - dithionite, and for antimony (V) using a suitable reductant such as potassium iodide, and with or without the purging from the solution of the excess of any gaseous reductant. Chemical reduction, however, is cumbersome and expensive and electrochemical reduction is much preferred.

At relatively high values of the applied current (and corresponding values of current density), the cathode becomes fully covered with deposited zinc and values of the cpp for zinc deposition on zinc are measured. At the high current values, the antimony (V) is electrochemically reduced and the sensivity of the method is high. This electrochemical reduction occurs in spite of the presence of any oxidizing agent, such as oxidized manganese species, which causes oxidation of antimony to its pentavalent state.

In order to measure values of the cpp on the moving cathode, it is necessary to expose the cathode to the high current for a length of time sufficient to cause full coverage of the cathode with deposited zinc. This sufficiently long time can be achieved by moving the cathode through the electrolyte at low speeds.

Values of the current density, giving values of the cpp in the desired range and ensuring good sensitivity of the method in the presence of Sb (V) in the electrolyte, are in the range of about 0.01 to 0.20 A/cm$^2$, Below 0.01 A/cm$^2$ the deposition of Zn does not give full coverage of the cathode with deposited zinc, while above 0.2 A/cm$^2$ gas evolution becomes significant. Preferred values of the current density are in the range of about 0.05 to 0.10 A/cm$^2$. The most preferred value is the value about equivalent to the current density used in the electrowinning process. The value of the applied current is preferably controlled at a substantially constant value.

The sensitivity of the method according to the invention is dependent on a sensitivity factor, which can be represented by the following equation:

Sensitivity Factor $= I \times L/S$, wherein
I = the current density in A/cm$^2$
L = length of the immersed length of the cathode exposed to electrolyte in cm; and
S = the speed of the moving cathode in cm/min.

The method can be operated with a sensitivity factor in the range of about 0.5 to 4.0. The use of a value of the Sensitivity Factor in the range of about 1.5 to 4.0 provides a sensitivity to antimony which is essentially the same when it is present in either the trivalent state or the pentavalent state.

In order to achieve a value of the sensitivity factor in the range of about 1.5 to 4.0, values for the current density (I) are in the range of about 0.05 to 0.10 A/cm$^2$, values for the length of immersed cathode (L) are in the range of about 2 to 4 cm, and values for the speed of the moving cathode (S) are in the range of 0.1 to 0.2 cm/min.

The temperature of the electrolyte being measured is preferably maintained constant because temperature changes affect the measured cpp. Suitable tempteratures are in the range of about 0° to 100° C., preferably 20° to 75° C.

The cpp is measured continuously or intermittently and is recorded on a suitable read-out instrument, or, alternatively, as a function of time on calibrated paper. For practical application of the method of this invention, the cpp is expressed as the value of the measured cpp at a current corresponding to the above recited current densities in the range of about 0.01 to 0.20 A/cm$^2$, preferably 0.05 to 0.10 A/cm$^2$. The recorded values of the cpp are maintained in a preferred range. This is accomplished by making adjustments to the purification and electrowinning processes when measured values of the cpp deviate from the preferred range of values. The values of the preferred range depends on a number of factors which are related to each particular process used for the recovery of zinc.

The cpp has specific values dependent on the composition of the electrolyte. As every electrolyte composition can be purified to an optimum degree, has an optimum range of polarization affecting agent(s) contents and has an optimum range of polarization affecting agent(s) contents relative to its impurity content, the cpp will similarly have a range of values to yield the desired optimum results. Anyone of a number of suitable polarization affecting agents may be used, for example, glue. Increasing concentrations of impurities cause a decrease in the cpp, while increasing polarization agent concentrations increase the cpp and increasing de-polarization agent concentrations decrease the cpp.

If the value of the measured cpp in the purification of electrolyte is too low, the impurity concentration is too high for optimum zinc recovery in the electrowinning proces. Thus, dependent on the composition of the electrolyte, the cpp is an indicator of the effectiveness of the purification process and deviations from optimum operation can be corrected by adjusting the purification process in relation to values of the cpp, whereby the impurity concentration is lowered. Correction of a zinc dust purification may be accomplished, for example, by adjusting the temperature or the duration, increasing the amount of zinc dust, or increasing the concentration of a depolarization agent such as antimony, copper, or arsenic in ionic form. Alternatively, insufficiently purified electrolyte may be further purified in an additional purification step or by recirculation in the purification process.

If the value of the cpp measured for the electrolyte in the electrowinning process is too low, the concentration of polarization affecting agent(s) in the electrolyte is too low to adequately control cathodic zinc resolution caused by the impurities present, or the impurity concentration is too high relative to the concentration of polarization affecting agent(s).

On the other hand, if the value is too high, the concentration of polarization affecting agent(s) is too high relative to the impurity concentration, and a resultant loss in current efficiency and a rougher zinc deposit occur. Thus, depending on the composition of the electrolyte, the cpp is an indicator of the efficiency of the electrowinning process and deviations from optimum operation can be corrected by changing the concentration of polarization affecting agent(s) or the concentration of impurities in the electrolyte as required in relation to values of the cpp, or by changing the concentration ratio between polarization affecting agent(s) and impurities in the electrolyte as required in relation to the values of the cpp. Change in the concentration of polarization affecting agent(s) may be accomplished in a suitable manner such as by increasing or decreasing the rate of addition of polarization affecting agents to the electrolyte. A decrease in the impurity concentration may be achieved by more effective purification of the electrolyte prior to the electrowinning process. In the case of the presence of an excess concentration of polarizing agent, corrective action may also be taken by adding a de-polarizing agent, such as antimony in ionic form to the electrolyte in a controlled fashion to bring the ratio of concentrations of impurities and polarization affecting agent(s) to the correct value.

For example, for a certain electrolyte composition, when the polarization affecting agent is animal glue, the concentration ratio can be adjusted by adjusting the concentration of glue to a value at which the cpp, when measured at a temperature between 25° and 40° C., a constant current value in the range of corresponding current density values of 0.05 to 0.10 $A/cm^2$ based on the exposed area of the cathode and a sensitivity factor in the range of about 1.5 to 4.0, is in the range of about 60 to 120 mV. The concentration of glue can be increased when the value of the cpp decreases below about 60 mV and decreased when the value of the cpp increases above about 120 mV, whereby the value of the measured cpp returns to within the range of 60 to 120 mV. Alternatively, when the polarization affecting agent is animal glue, the concentration ratio can be adjusted by adjusting the concentration of antimony to a value at which the cpp, when measured between 25° and 40° C., 0.05 and 0.10 $A/cm^2$ and a sensitivity factor of from 1.5 to 4.0, is in the range of 60 to 120 mV. The concentration of antimony is increased when the cpp value rises above 120 mV and decreased when the cpp value decreases below 60 mV, whereby the value of the measured cpp returns to within the range of 60 to 120 mV. It is understood that the desired ranges of the cpp values can have different values for different electrolyte compositions.

The method of the invention has a number of applications in the process for the recovery of zinc from zinc sulfate electrolyte. Thus, the method can be used before, during and after purification of zinc sulfate electrolyte and before, during and after the electrowinning of zinc from zinc sulfate electrolyte.

For example, prior to the zinc dust purification process, the method can be used to determine the degree of iron oxide removal and the degree of removal by iron oxides of impurities such as arsenic, antimony and germanium from zinc sulfate solutions obtained in the leaching of ores, concentrates or calcines. During purification, the method can be used to determine the degree of purification obtained, for example, with zinc dust, in the various steps of the purification process. After purification, the effectivenss of the purification can be determined, as well as the possible need for adjustments to the purification process or to the subsequent electrowinning process, In the electrowinning process, the method can be advantageously used to determine the required amount of polarization affecting agent(s) alone and in relation to impurity concentration, the required amount of impurities in relation to concentration of polarization affecting agent(s), the need for adjustments to the electrolyte feed, or to electrolyte in process and the quality of recycled electrolyte.

The invention will now be described by means of the following non-limitative examples:

The method of the invention used in the following examples for determining the cpp comprised flowing a sample of electrolyte at a constant rate of 60 ml/min through a test cell having a volume of 125 ml. The electrolyte was maintained at 35° C.+0.05° C. by passage through a temperature controlled heating block before entering the test cell. Aluminum foil, in the shape of a continuous strip 0.6 cm wire, was introduced into the electrolyte and was passed around a half immersed Teflon pulley with a diameter in the range of 0.3 to 2.5 cm. The foil was withdrawn continuously using an electrical drive mechanism capable of operation such that the foil could move with speeds in the range of 0.1 to 2 cm/min. A platinum-coated titanium anode and an SCE were positioned in the electrolyte for polarization and reference respectively. The electrodes were positioned in fixed positions in the electrolyte, the SCE positioned between cathode and anode. The immersed surface of the cathode was 4 cm away from the surface of the anode and the tip of the SCE was 2.5 cm away from the cathode. A constant current in the range of 0.5 to 200 mA generated with a galvanostat was passed through the cell and values of the cpp were measured between the cathode and the SCE, having been corrected for the values of the IR voltage drop between the reference electrode and the cathode and that of the reversible potential of zinc, and recorded. The IR voltage drop was measured by the well-known rapid interruptor technique using an Electrosynthesis Company Model 800 measurement instrument, (See Transient Techniques in Electrochemistry, Digby MacDonald, Plenum Press, New York, 1977.)

EXAMPLE 1

With a 0.3 cm diameter Teflon pulley, the aluminum foil moving at 1 cm/min, and an applied current of 0.7 mA, the cpp for a zinc electrolyte containing as major components 150 g/l $H_2SO_4$ and 55 g/l Zn was measured to be 116 mV. Addition of 0.02 ppm antimony as antimony tartrate to the electrolyte yielded upon remeasurement a cpp of 85 mV. Following addition of 100 ppm of potassium permanganate to oxidize the antimony and to raise the oxidation potential of the electrolyte to 1.2 V versus SCE, the cpp was again measured and found to be 105 mV, thus indicating that under the conditions used the sensitivity to antimony was less in the oxidized than in the reduced state.

EXAMPLE 2

Using the same diameter pulley as in Example 1 and the same electrolyte and conditions, but with movement of the foil through the electrolyte at 0.1 cm/min, the cpp for the electrolyte without additions was measured to be 102 mV. After the addition of 0.02 ppm antimony as antimony tartrate, the cpp was measured to be 82 mV. Following the addition of 100 ppm KMnO4 to the antimony-containing electrolyte, the cpp was found to have risen to 90 mV. The above experiment shows that the effect of decreasing the foil speed at low current densities was to decrease the response to antimony as Sb (III). The sensitivity to antimony (V) was also not increased by operating it slower rather than faster foil speeds when the polarization current was small, as used in this experiment.

EXAMPLE 3

With a 2.5 cm diameter Teflon pulley, the aluminum foil moving at 1.0 cm/min and with an applied current of 100 mA, the cpp versus S.C.E. for the same electrolyte as in Examples 1 and 2, was found to be 54 mV. Addition of 0.02 ppm antimony as antimony tartrate gave a cpp of 28 mV upon remeasurement. Following the addition of 100 ppm KMnO4 to the antimony-containing electrolyte, the cpp was again measured and found to be 38 mV. These results indicate that use of a larger diameter pulley and ptolarization current higher than used in Examples 1 and 2, has increased the sensitivity of the method to antimony (V).

EXAMPLE 4

With the same Teflon pulley as used in Example 3, the aluminum foil moving at 0.1 cm/min and an applied current of 158 mA, the cpp versus SCE, for the same electrolyte as in Examples 1, 2 and 3, was found to be 60 mV. Addition of 0.02 ppm antimony as antimony tartrate gave a cpp of 32 mV upon remeasurement. Following the addition of 100 ppm KMnO4 to the antimony-containing electrolyte, the cpp was again measured and found to be 32 mV. Ths result indicates that the use of a large Teflon pulley, high applied currents, and slow foil speeds, eliminates the depressing effect of oxidation on the sensitivity of the method to antimony.

EXAMPLE 5

Experiments were made with Teflon pulleys of 0.32 cm, 1.25 cm and 2.54 cm diameter, with aluminum foil speeds of 0.1 and 1 cm/min and current densities from 13 to 111 mA/cm$^2$. The sensitivity factor was calculated according to the equation already given and these values are shown in Table I together with the corresponding values of $\Delta_1$, which is the difference between the cpp with antimony in the oxidized and the reduced states. The results show that, as the sensitivity factor is increased, the difference between the cpp for the two states of oxidation of antimony is decreased until it becomes negligible in the range of 2 to 3.

TABLE I

| Sensitivity Factor vs $\Delta_1$ | | | | |
|---|---|---|---|---|
| Pulley Diameter (cm) | Speed (cm/min) | Current Density (mA/cm$^2$) | Sensitivity Factor A-min/cm$^2$ | $\Delta_1$ (mV) |
| 2.54 | 0.1 | 79 | 3.16 | 0 |
| 1.25 | 0.1 | 111 | 2.22 | 1 |
| 1.25 | 0.1 | 55 | 1.10 | 4 |
| 1.25 | 0.1 | 39 | 0.79 | 6 |
| 2.54 | 1.0 | 55 | 0.22 | 12 |
| 0.32 | 1.0 | 13 | 0.02 | 20 |

EXAMPLE 6

Experiments were made with a Teflon pulley of 2.5 cm diameter, with an aluminum foil speed of 0.1 cm/min and with current densities ranging between 20 and 120 mA/cm$^2$. Values of the cpp were measured with a zinc electrolyte which initially contained essentially no antimony. Antimony was then added as antimony tartrate to give a concentration of 0.02 ppm antimony as Sb (III) and the cpp values again determined. The values of $\Delta_2$, the difference between the cpp values in the absence and presence of antimony at different current densities (Table II) show that the sensitivity to Sb (III) increases with increasing current density. The results of these experiments, when considered with those of Example 5, show that, by selection of an appropriate sensitivity factor and a high current density, the sensitivity to Sb (III) increases with increasing current density.

TABLE II

| Current Density vs $\Delta_2$ | | | |
|---|---|---|---|
| Pulley Diameter (cm) | Speed (cm/min) | Current Density (mA/cm$^2$) | $\Delta_2$ (mV) due to Sb$^{3+}$ |
| 2.54 | 0.1 | 24 | 14 |
| 2.54 | 0.1 | 55 | 22 |
| 2.54 | 0.1 | 118 | 32 |

EXAMPLE 7

A number of tests were carried out in which electrolytes each with a different cpp value, were circulated through the test cell and then through an electrolytic cell wherein zinc was plated onto an aluminium cathode. The cpp values were determined with a cathode speed of 0.1 cm/min., an applied current of 158 mA and a pulley diameter of 2.5 cm. After 24 hours of plating, the current efficiency for zinc deposition was determined. The cpp value and the current efficiency for each test is given in Table III.

TABLE III

| Test Number | CPP in-mV | Current Efficiency |
|---|---|---|
| 1 | 51 | 74.0 |
| 2 | 65 | 89.0 |
| 3 | 75 | 91.3 |
| 4 | 82 | 91.5 |
| 5 | 85 | 89.5 |
| 6 | 90 | 87.5 |

The results show that in these tests the maximum current efficiency was obtained at cpp values in the range of 75 to 85 mV. It also follows from these tests that the method according to the invention can be used to detect the best conditions for the plating of zinc.

The embodiments of the invention in which an exclusive property or privilege is claimed are defined as follows:

1. A method for controlling a process for the electrolytic recovery of zinc using a zinc sulfate electrolyte containing concentrations of impurities, including pentavalent antimony, and at least one polarization affecting agent, said method comprising the steps of:
   (i) establishing a test circuit comprising in combination a test cell, a sample of electrolyte, an elongated moving cathode made of an electrolytically conductive material on which zinc is deposited, which moving cathode is immersed in and passes through said sample at a predetermined speed and has a predetermined determined area exposed to said electrolyte, an anode and a reference electrode also immersed in said sample, all three electrodes being removably positioned in the test cell in fixed relation to one another, a constant current supply and a voltage measuring means electrically connected to said electrodes;
   (ii) applying a substantially constant current to the electrodes in said test cell, said current corresponding to a current density in the range of about 0.01 to 0.20 A/cm² based on the area of the moving cathode exposed to electrolyte in the test cell, and being sufficient to cause the exposed area of the cathode to become fully covered with deposited zinc;
   (iii) moving said cathode at a predetermined speed sufficient to obtain measured values of the cathode polarization potential for zinc deposition onto zinc, under conditions such that the current density, immersed length of cathode, and the speed of the moving cathode provide a sensitivity factor having a value within the range of about 0.5 to 4.0 when calculated in accordance with the following equation:

Sensitivity Factor = $I \times L/S$ wherein
   I represents current density, in A/cm²;
   L represents the immersed length of the moving cathode exposed to electrolyte, in cm; and
   S represents the speed of the moving cathode, in cm/min;
   (iv) measuring the cathode polarization potential for zinc deposition onto zinc;
   (v) relating the values of the measured cathode polarization potential to the concentrations of the impurities or the polarization affecting agent or the ratio between the two in said sample; and
   (vi) adjusting the concentrations of the impurities or the polarization affecting agent or the ratio between the two in the electrolyte of the process for the electrolytic recovery of zinc to obtain optimum recovery of zinc.

2. A method as claimed in claim 1, wherein said process is the process for the electrowinning of zinc and wherein values of the measured cathode polarization potential are related to the concentration of said at least one polarization affecting agent in said sample; and the concentration of said agent in the electrolyte of the process for the electrowinning of zinc is adjusted to obtain optimum efficiency and level zinc deposits.

3. A method as claimed in claim 2, wherein values of the measured cathode polarization potential for zinc deposition onto zinc are related to the concentration ratio between impurities and said at least one polarization affecting agent in said sample; and the concentration ratio between said impurities and said at least one polarization affecting agent in the electrolyte of the process for the electrowinning of zinc is adjusted to obtain optimum efficiency and level zinc deposits.

4. A method as claimed in claim 3 wherein the concentration ratio is adjusted by changing the concentration of impurities in the electrolyte.

5. A method as claimed in claim 3 wherein the concentration ratio is adjusted by changing the concentration of polarization affecting agents in the electrolyte.

6. A method as claimed in claim 3 wherein the concentration ratio in the electrolyte is adjusted by changing the concentration of the impurities and the concentration of said at least one polarization affecting agent.

7. A method as claimed in claim 3, wherein the polarization affecting agent is animal glue, the concentration ratio is adjusted by adjusting the concentration of glue to a value at which the cathode polarization potential measured at a temperature of between 25° C. and 40° C. is in the range of about 60 to 120 millivolts, the cathode polarization potential is measured at a value of the substantially constant current which corresponds to a value of current density in the range of about 0.05 to 0.10 A/cm² based on the exposed area of the moving cathode, and the sensitivity factor is in the range of about 1.5 to 4.0.

8. A method as claimed in claim 7, wherein the concentration of glue is increased when the value of the measured cathode polarization potential for zinc deposition onto zinc decreases below about 60 mV and wherein the concentration of glue is decreased when the value of the measured cathode polarization potential for zinc deposition onto zinc increases above about 120 mV, whereby the value of the measured cathode polarization potential for zinc deposition onto zinc returns to within the range of about 60 mV to 120 mV.

9. A method as claimed in claim 3, wherein the polarization affecting agent is animal glue, the concentration ratio is adjusted by adjusting the concentration of antimony to a value at which the cathode polarization potential measured at a temperature in the range of 25° to 40° C. is in the range of about 60 to 120 mV, the cathode polarization potential is measured at a value of the substantially constant current which corresponds to a value of current density in the range of about 0.05 to 0.10 A/cm² based on the exposed area of the moving cathode, and the sensitivity factor in the range of about 1.5 to 4.0.

10. A method as claimed in claim 9, wherein the concentration of antimony is increased wherein the value of the measured cathode polarization potential for zinc deposition onto zinc increases above about 120 mV and wherein the concentration of antimony is decreased when the value of the measured cathode polarization potential decrease below about 60 mV, whereby the value of the measured cathode polarization potential for zinc deposition onto zinc returns to within the range of about 60 mV to 120 mV.

11. A method as claimed in claim 3 wherein the concentration of said at least one polarization affecting agent is adjusted by either increasing the amount of agent already present, or by adding a polarization affecting agent of polarization affecting characteristics opposite to that of the polarization affecting agent already present.

12. A method as claimed in claim 3, wherein the current, expressed as current density, is in the range of about 0.05 to 0.10 A/m² the sensititivity factor is in the range of about 1.5 to 4.0, the electrolyte in the test cell is kept at a substantially constant temperature in the range of about 20° to 75° C., the electrolyte in the test cell is kept in motion by continuously passing a flow of electrolyte through said test cell, the elongated moving cathode in the test cell is a strip, wire, or foil made of a material chosen from aluminum and aluminum alloys, and the elongated cathode is continuously passed through said sample of electrolyte at a substantially constant predetermined speed.

13. A method as claimed in claim 2 wherein the concentration of said at least one polarization affecting agent is adjusted by either increasing the amount of agent already present, or by adding a polarization affecting agent of polarization affecting characteristics opptosite to that of the polarization affecting agent already present.

14. A method as claimed in claim 2, wherein the current, expressed as current density is in the range of about 0.05 to 0.10 A/cm², the sensitivity factor is in the range of about 1.5 to 4.0, the electrolyte in the test cell is kept at a substantially constant temperature in the range of about 20° to 75° C.; the electrolyte in the test cell is kept in motion by continuously passing a flow of electrolyte through said test cell; the elongated moving cathode in the test cell is a strip, wire, or foil made of a material chosen from aluminum and aluminum alloys; and the elongated moving cathode is continuously passed through said sample of electrolyte at a substantially constant predetermined speed.

15. A method as claimed in claim 1, wherein the current expressed as current density is in the range of about 0.05 to 0.10 A/cm², the moving cathode is advanced through the sample of electrolyte at a substantially constant rate, and the sensitivity factor is in the range of about 1.5 to 4.0.

16. A method as claimed in claim 1, wherein the current, expressed as current density, is in the range of about 0.05 to 0.10 A/m², the sensitivity factor is in the range of about 1.5 to 4.0, the electrolyte in the test cell is kept at a substantially constant temperature in the range of about 20° to 75° C., the electrolyte in the test cell is kept in motion by continuously passing a flow of electrolyte through said test cell, the elongated moving cathode in the test cell is a strip, wire, or foil made of a material chosen from aluminum and aluminum alloys, and the elongated cathode is continuously passed through said sample of electrolyte at a substantially constant predetermined speed.

* * * * *